(12) United States Patent
Gazzaniga et al.

(10) Patent No.: US 8,367,043 B2
(45) Date of Patent: Feb. 5, 2013

(54) BIOLOGICALLY ACTIVE NANOPARTICLES A CARBONATE-SUBSTITUTED HYDROXYAPATITE, PROCESS FOR THEIR PREPARATION AND COMPOSITIONS INCORPORATING THE SAME

(75) Inventors: Giancarlo Gazzaniga, Salice Terme (IT); Norberto Roveri, Bologna (IT); Lia Rimondini, Bologna (IT); Barbara Palazzo, Bologna (IT); Michele Iafisco, Bologna (IT); Paolo Gualandi, Castelmaggiore (IT)

(73) Assignee: Coswell S.p.A., Funo di Argelato (BO) (IT)

( * ) Notice: Subject to any disclaimer, the term of this patent is extended or adjusted under 35 U.S.C. 154(b) by 1061 days.

(21) Appl. No.: 11/916,022
(22) PCT Filed: May 30, 2006
(86) PCT No.: PCT/EP2006/005146
  § 371 (c)(1),
  (2), (4) Date: Apr. 22, 2008
(87) PCT Pub. No.: WO2007/137606
  PCT Pub. Date: Dec. 6, 2007

(65) Prior Publication Data
  US 2009/0130150 A1    May 21, 2009

(51) Int. Cl.
  *A61K 6/00* (2006.01)
  *A61K 6/033* (2006.01)
  *A61K 9/14* (2006.01)
  *A61Q 11/00* (2006.01)
  *C01F 11/00* (2006.01)
(52) U.S. Cl. .......... 424/49; 424/489; 424/675; 424/687; 977/773
(58) Field of Classification Search ........................ None
  See application file for complete search history.

(56) References Cited

U.S. PATENT DOCUMENTS 5,468,489 A * 11/1995 Sakuma et al. ................. 424/49
6,358,494 B1 * 3/2002 Aoki et al. ...................... 424/52
(Continued)

FOREIGN PATENT DOCUMENTS

CA    999 238    11/1976
(Continued)

OTHER PUBLICATIONS

E Landi, G Celotti, G Logroscino, A Tampieri. "Carbonated Hydroxyapatite as Bone Substitute." Journal of the European Ceramic Society, vol. 23, 2003, pp. 2931-2937.*

(Continued)

*Primary Examiner* — Brian Gulledge
*Assistant Examiner* — Isaac Shomer
(74) *Attorney, Agent, or Firm* — Steinfl & Bruno LLP

(57) ABSTRACT

The invention relates to biologically active nanoparticles of a carbonate-substituted non-stoichiometric hydroxyapatite, having:
a) a crystallinity degree CD lower than 40%, the crystallinity degree being defined as $$CD = (1 - X/Y) \cdot 100$$

wherein: Y=height of the diffraction maximum at 2θ=33°, X=height of the diffraction background at 2θ=33° of the nanoparticles X-ray diffraction pattern;
b) a length L ranging from 20 to 200 nm and a width W ranging from 5 to 30 nm; and
c) an aspect ratio AR comprised between 2 and 40, the aspect ratio being defined as AR=L/W.

The biologically active nanoparticles of the invention find a preferred use in oral or dental hygiene applications and may be formulated as compositions for oral or dental hygiene such as, for example, solutions, suspensions, oils, gels or other solid products. Other aspects of the invention include a process for preparing a suspension for oral or dental hygiene including the aforementioned biologically active nanoparticles, a process for manufacturing a toothpaste comprising the nanoparticles, as well as a method of locally remineralizing the teeth comprising contacting the teeth with the nanoparticles.

49 Claims, 6 Drawing Sheets

U.S. PATENT DOCUMENTS

| | | | |
|---|---|---|---|
| 7,320,728 | B2 | 1/2008 | Noerenberg et al. |
| 2004/0250729 | A1* | 12/2004 | Jang et al. .................. 106/35 |
| 2007/0154411 | A1 | 7/2007 | Barth et al. |

FOREIGN PATENT DOCUMENTS

| | | |
|---|---|---|
| EP | 0 539 651 | 5/1993 |
| EP | 066 4133 | 7/1995 |
| EP | 0 723 773 | 7/1996 |
| WO | 99/32400 | 7/1999 |
| WO | 00/03747 | 1/2000 |
| WO | 2005/005815 | 1/2005 |
| WO | 2005/082780 | 9/2005 |

OTHER PUBLICATIONS

IY Saleem, M Vordermeier, JE Barralet, AGA Coombes. "Improving peptide-based assays to differentiate between vaccination and *Mycobacterium bovis* infection in cattle using nanoparticle carriers for adsorbed antigens." Journal of Controlled Release, vol. 102, 2005, pp. 551-561.*

JE Barralet, S Aldred, AJ Wright, AGA Coombes. "In Vitro Behavior of Albumin-Loaded Carbonate Hydroxyapatite Gel." J. Biomed. Mater. Res., vol. 60, 2002, pp. 360-367.*

A Yasukawa, K Kandori, T Ishikawa. "TPD-TG-MS Study of Carbonate Calcium Hydroxyapatite Particles." Calcified Tissue International, vol. 72, 2003, pp. 243-250.*

M Okazaki, Y Moriwaki, T Aoba, Y Doi, J Takahashi. "Solubility Behavior of CO3 Apatites in Relation to Crystallinity." Caries Research, vol. 15, 1981, pp. 477-483.*

PCT International Search Report for PCT/EP2006/005146 filed on May 30, 2006 in the name of CoswellS.P.A, et al.

Stephen Brunauer, et al. "Adsorption of Gases in Multimolecular Layers" in J. Am. Chem. Soc. 60 (1938) pp. 309-319.

Z.E. Erkmen "The effect of heat treatment on the morphology of D-Gun Sprayed Hydroxyapatite coatings" in J. Biomed. Mater Res [Appl Biomaterial] 48; 861-868, 1999.

S.J.Gregg et al. "Adsorption, Surface Area and Porosity",2nd Edition; Academic Press 1982; ISBN 012300956-1.

E. Landi, et al. "Densification behaviour and mechanics of synthetic hydroxyapatites" in Journal of the European Ceramic,Society 20 [2000]pp. 2377-2387.

I.Mayer et al. "Dissolution studies of Zn-containing carbonated hydroxyapatites" in the Journal of Crystal Growth 219 [2000] pp. 98-100.

Written Opinion for PCT/EP2006/005146 filed on May 30, 2006 in the name of Guaber S.P.A.

Okazaki, M. et al. Solubility behavior of CO3 apatites in relation to crystallinity. Caries Research, vol. 15, Issue 6, pp. 477-83 (1981)—Abstract Only.

Office Action issued by the State Intellectual Property Office of the People's Republic of China for Chinese Application No. 200680055372.8 dated Dec. 27, 2010.

Office Action issued by Russian Patent and Trademark Agency for Russian Application No. 2008149915/15(065503) dated Jan. 18, 2010.

Office Action issued by the Ministry of Science and Education of Ukraine—State Deparatment of Intellectual Property for Ukrainian Application No. .a200814940 dated Jul. 14, 2010.

* cited by examiner

BIOLOGICALLY ACTIVE NANOPARTICLES A CARBONATE-SUBSTITUTED HYDROXYAPATITE, PROCESS FOR THEIR PREPARATION AND COMPOSITIONS INCORPORATING THE SAME

CROSS REFERENCE TO RELATED APPLICATIONS

This application is the national phase of International Application PCT/EP2006/005146 filed on May 30, 2006.

FIELD OF THE INVENTION

The invention relates to biologically active nanoparticles of a carbonate-substituted hydroxyapatite, to a process for their preparation and to compositions incorporating the same.

More specifically, the invention relates to biologically active nanoparticles which find a preferred although not exclusive use in oral or dental hygiene applications, as well as to compositions for oral or dental hygiene which include the same such as, for example, solutions, suspensions, oils, gels or other solid products.

According to other aspects, the invention relates to a process for preparing a suspension for oral or dental hygiene, to a process for manufacturing a toothpaste comprising the aforementioned biologically active nanoparticles, as well as to a method of locally remineralizing the teeth comprising contacting the teeth with the nanoparticles.

BACKGROUND OF THE INVENTION

It is known that a high proportion of the population, estimated by the dental profession to be in the region of 20 to 25% of the total population, suffers from hypersensitivity or hyperaesthesia of the teeth, in other words pain in response to mechanical, chemical and thermal stimuli, without any visible dental diseases such as caries which would require dental treatment.

The hypersensitivity of the teeth occurs mainly at the neck of the teeth when the soft dentine becomes exposed between the boundary of the enamel and the gum line due to recession of the gums. The action of lactic acid forming lactobacilli or the mechanical action of braces (even in children) or the engaging parts of dentures during chewing may also damage the protective enamel so that the dentinal canaliculi which are then exposed transmit every mechanical, chemical or thermal irritation as a painful stimulus to the tooth pulp.

RELATED ART

It is known that repeated treatment with inorganic salts, particularly sodium bicarbonate, sodium chloride or strontium chloride at high concentrations in the presence of glycerine desensitizes the sensitive parts of the teeth but that this desensitization is reversible so that pain is again felt soon after therapy has stopped.

In order to treat in a more permanent way these painful conditions in the course of the normal routine of dental hygiene of a suffering individual, it has then been proposed in the art to provide oral or dental preparations capable to improve the desensitization effect by providing a long lasting remineralisation of the teeth.

Thus, for example, Canadian patent CA 999 238 discloses an oral or dental preparation containing 5 to 90% by weight of finely divided hydroxyapatite having an average particle size of less than 10 µm, in particular in the region of about 6 to 8 µm.

According to this reference, if this finely divided hydroxyapatite is repeatedly brought into contact with sensitive teeth over a prolonged period of time, for example when cleaning the teeth or when chewing a chewing gum, a long lasting remineralisation of the teeth may be achieved thanks to the diffusion of the hydroxyapatite into the exposed dentinal canaliculi by virtue of its very slight solubility in water and saliva due to hydrolysis. Accordingly, this sparingly soluble hydroxyapatite becomes deposited in the microscopically fine cavities left in the hydroxyapatite structure which has been formed in the organic matrix, so that the dentinal canaliculi are gradually sealed and permanent relief from pain is obtained.

Apart from the above-identified problem of hypersensitivity or hyperaesthesia of the teeth, it is also known that many people suffer from chronic bleeding of the gums, a consequence of gingivitis, deposits of secretions from the gingival crevices and lesions in the bed of the teeth, which in advanced stages result in loosening or loss of teeth and in loss of the tooth bed. Anaerobic putrefactive bacteria which cause halitosis are able to multiply rapidly in the protective environment of the inflamed and secretion-depositing tissue so that they easily give rise to inflammation of the buccal mucous membrane and even irritation of the pharyngeal cavity.

In order to treat in some way these teeth and gums disorders and in general to increase oral hygiene in the course of the normal routine of dental washing, it has been proposed in the art to provide oral or dental preparations capable to exploit an antibacterial effect. Thus, for example, European patent application EP 0 539 651 discloses a dentifrice (tooth paste or powder) in which an antibacterial material (metal-ion agent) is stably and firmly carried or supported by a carrier as a component of the dentifrice.

More specifically, this reference discloses a dentifrice containing a calcium compound, such as hydroxyapatite, in the form of a powder having an antibacterial metal carried by the calcium compound in a highly stable way so as to prevent the toxicity due to the ion form of the metal while contributing to a medical treatment of teeth and further providing the dentifrice with a good preservability for a long period of time.

In recent times and based on the fact that the teeth bone tissue is primarily constituted by non-stoichiometric hydroxyapatite containing specific substituting ions at both the cationic and anionic reticular sites, the use of nanoparticles of a hydroxyapatite compound has been proposed for the treatment of bone defects in the fields of reconstructive bone surgery, surgical stomatology, traumatology, orthopedics and dentistry.

Thus, for example, European patent application EP 0 664 133 discloses a preparation for stimulating growth in bone tissue based on hydroxyapatite, wherein the hydroxyapatite is taken in the form of an aqueous pasta with a concentration of 18-36% by weight with a particle size of 15 to 60 nm.

According to this reference, such a preparation when applied and left to interact with the bone tissue to be repaired for an extended period of time, acts as a stimulator of the proliferative and biosynthetic activity of the osteoblasts.

International patent application WO 2005/05815, on the other hand, discloses magnesium-containing carbonated hydroxyapatite (MgCHA) suitable for creating a compound material in the form of a freeze-dried granulate suitable for bone implants, particularly in the field of dentistry, consisting of said modified hydroxyapatite and an organic polymer, preferably an alginate.

According to this reference, a compound material including such a modified hydroxyapatite is capable of efficiently repairing bone defects following application and interaction with the bone tissue for an extended period of time of the necessary amount of product at the level of the existing cavity in the bone.

The present inventors have observed that the hydroxyapatite compounds and compositions of the prior art have a limited effect in the treatment of teeth hypersensitivity in the course of the normal routine of dental hygiene.

The cleaning operations of the teeth by means of a toothpaste or the rinsing operations of teeth and mouth by means of a mouthwash or gargle, even if prolonged, may extend over a period of time which is quite limited and insufficient for the known hydroxyapatite compounds and for its optional additional components to fully exert their desensitizing and optionally antimicrobial effects.

SUMMARY OF THE INVENTION

According to one aspect thereof, the present invention therefore provides a biologically active hydroxyapatite compound capable of effectively improving teeth desensitization and remineralisation even in the limited time available during the normal routine of dental hygiene.

Biologically active nanoparticles of a carbonate-substituted hydroxyapatite according to the invention are defined in attached claim 1.

More specifically, the biologically active nanoparticles of the invention are nanoparticles of a carbonate-substituted non-stoichiometric hydroxyapatite, having:
a) a crystallinity degree CD lower than 40%, the crystallinity degree being defined as $$CD = (1 - X/Y) \cdot 100$$

wherein:
Y=height of the diffraction maximum at 2θ=33°, X=height of the diffraction background at 2θ=33° of the nanoparticles X-ray diffraction pattern;
b) a length L ranging from 20 to 200 nm and a width W ranging from 5 to 30 nm; and
c) an aspect ratio AR comprised between 2 and 40, the aspect ratio being defined as $$AR = L/W$$

The inventors have observed that the nanoparticles of carbonate-substituted hydroxyapatite having the aforementioned features possess a high affinity to the mineral components of teeth dentine and enamel and are capable of "mimicking" the structure of these components to the extent that the nanoparticles are capable of effectively interact with the dentine and enamel surface.

The inventors have also observed that the nanoparticles of carbonate-substituted hydroxyapatite of the invention achieve at the same time an enhanced reactivity with the dentine and enamel surface which is effectively exploited even in the limited time available during the normal routine of dental hygiene.

Although the inventors do not wish to be bound by any theory, it is believed that this enhanced activity is due to a combination of factors which mimic biogenic hydroxyapatite nanoparticles, such as a suitable non-stoichiometric composition of the hydroxyapatite, an extremely reduced size (nanoscale) and a consequent high surface area of the non-stoichiometric hydroxyapatite compound, a low crystallinity degree of the same and an elongated shape (as defined by their aspect ratio), which promote both an increased solubility and an enhanced affinity to the mineral components of teeth dentine and enamel.

More specifically, it is believed that a major role in enhancing the reactivity of the nanoparticles of the invention is played by the elevated surface disorder of their outer surface at which the ions stoichiometry of the bulk portion of the particles is no longer maintained.

For the purposes of the present description and of the claims which follow, the term: nanoparticle, is used to indicate a particle having a size generally below 1 μm; preferably, the nanoparticles of the invention have a flattened acicular shape which is most adapted to interact with the dentine and enamel surface.

For the purposes of the present description and of the claims which follow, the expression: biologically active, is used to indicate the capability of a substance or composition of interacting with the teeth dentine and/or enamel and/or gums and/or the other oral tissues.

For the purposes of the present description and of the claims which follow, the expression: crystallinity degree, is intended to indicate the percentage of the hydroxyapatite compound present in the crystalline state.

For the purposes of the invention, the crystallinity degree can be measured according to known methods, such as, for example, by using x-ray diffraction analysis.

Within the framework of the definition given above, the crystallinity degree CD is measured according to the method described in: Landi, E., Tampieri, A., Celotti, G., Sprio, S., *"Densification behaviour and mechanisms of synthetic hydroxyapatites"*, J. Eur. Ceram. Soc., 2000, 20, 2377-2387 (hereinafter in short: the Landi et al. method). The crystallinity degree of the nanoparticles can be also be evaluated according to the alternative method reported by Z. E. Erkmen *"The effect of heat treatment on the morphology of D-Gun Sprayed Hydroxyapatite coatings"*, J. Biomed Mater Res (*Appl Biomaterial*) 48; 861-868, 1999 (hereinafter in short: the Erkmen method).

According to this alternative method, the crystallinity degree CD' may be defined as $$CD' = (X/Y) \cdot 100$$

wherein:
Y=diffracted peaks net area+background area, X=diffracted peaks net area of the nanoparticles X-ray diffraction pattern.

The numerical values of the crystallinity degree CD' measured according to Erkmen method differ from those of the Landi et al. method; in this instance, in fact, the crystallinity degree CD' of the nanoparticles of the invention is lower than 70%.

For the purposes of the present description and of the claims which follow, the expression: lower than, as used before any numerical value, is meant to exclude such a numerical value and used to encompass only a range of lower values.

For the purposes of the present description and of the claims which follow, the term: length L of the nanoparticles, is intended to mean the dimension of the nanoparticle as measured along the major axis thereof, while the term: width W of the nanoparticles, is intended to mean the dimension of the nanoparticle as measured along the minor axis thereof.

For the purposes of the invention, the length L and the width W of the nanoparticles can be measured according to known methods, such as, for example, by using transmission electron microscopy (TEM).

For the purposes of the present description and of the claims which follow, except where otherwise indicated, all numerical values expressing parameters such as amounts, weights, temperatures, percentages, and so forth, are to be understood as being modified in all instances by the term "about". Also, all ranges include any combination of the maximum and minimum points disclosed and include any intermediate ranges therein, which may or may not be specifically enumerated herein.

As mentioned above, the nanoparticles of the invention are nanoparticles of carbonate-substituted non-stoichiometric hydroxyapatite which incorporate carbonate ions in the apatite structure.

This feature advantageously enhances the biological activity of the nanoparticles, since the carbonate ion is also found in the structure of natural hydroxyapatite. In this regard, it is to be observed that the carbonate ion can occupy in two different sites in the natural hydroxyapatite structure: namely, it can partially substitute the OH-ion (site A) and/or the $PO_4^{3-}$ ion (site B). Both the total carbonate content (in the range of 3-8 wt. %) and the relative quantities of type A and type B carbonation (A/B in the range of 0.7-0.9) found in the natural carbonate-substituted hydroxyapatite depend on the age of the individual and on the biological localization of the calcified tissue.

In the nanoparticles of the invention, carbonation preferably takes place at site B, as this results in a reduction of the crystallinity and an increase of the solubility of the apatite phase.

In a preferred embodiment of the invention, the hydroxyapatite nanoparticles comprise from 1 to 15% by weight and, more preferably, from 1 to 10% by weight based on the total weight of the nanoparticles of carbonate substituted into the hydroxyapatite structure.

In this way, the biological activity of the nanoparticles is advantageously enhanced, since their structure more closely resembles the structure of the natural apatite present in the teeth tissues.

According to a preferred embodiment of the invention, the ratio A/B between the carbonate substitution at the hydroxyl site (A) and the carbonate substitution at the phosphate site (B) of the hydroxyapatite is comprised between 0.05 and 0.5 and, still more preferably, comprised between 0.18 and 0.33.

According to another preferred embodiment of the invention, the carbonate substitution at the phosphate site (B) of the hydroxyapatite is greater than or equal to 65% by weight and, still more preferably, comprised between 90% and 100% by weight, of the total carbonate present in the hydroxyapatite.

These preferred patterns of carbonate substitution in the hydroxyapatite structure advantageously allow to increase the solubility of the nanoparticles in a biological environment. Additionally, the carbonate substitution at the phosphate site (B) advantageously induces a higher affinity of the hydroxyapatite nanoparticles for the osteoblast cell, increasing cellular adhesion and collagen production.

According to a preferred embodiment of the invention, the nanoparticles have a crystallinity degree CD comprised between 25% and 35% as measured according to the Landi et al. method which corresponds to a crystallinity degree CD' comprised between 40% and 60% as measured according to the Erkmen method.

In this way, the biological activity of the nanoparticles may be advantageously enhanced, since their low crystallinity helps in promoting both an increased solubility and an enhanced affinity to the mineral components of teeth dentine and enamel. According to a preferred embodiment of the invention, the nanoparticles have a surface area comprised between 30 and 60 $m^2/g$.

In this way, the biological activity of the nanoparticles in terms of reactivity with the mineral components of teeth dentine and enamel may be advantageously enhanced.

For the purposes of the invention, the surface area of the hydroxyapatite compound can be measured according to known methods, such as, for example, by the BET method.

In connection with this parameter, the inventors have observed that the average values of the surface area of the nanoparticles may vary within the aforementioned range as a function of the total amount of nanoparticles synthesized per each production batch, the higher values being more easily reached the smaller is the entity of the production batch. As indicated above, the nanoparticles of the invention have a reduced size (a length L ranging from 20 to 200 nm and a width W ranging from 5 to 20 nm) as measured by the TEM technique, and an elongated shape as defined by an aspect ratio AR ranging from 2 to 40.

According to a preferred embodiment of the invention, the nanoparticles possess a substantially acicular or platelet shape having a length L comprised between 50 and 150 nm and a width W comprised between 5 and 20 nm.

Preferably, furthermore, the nanoparticles have a thickness T as measured by the TEM technique ranging from 2 to 15 nm.

The aspect ratio AR of the nanoparticles is preferably comprised between 2 and 16 and, still more preferably, between 5 and 10.

In this way, the biological activity of the nanoparticles may be advantageously enhanced, since the combination of reduced shape and elongate size helps in effectively sealing the dentinal canaliculi and achieving an effective permanent relief from pain even in the limited time available during the normal routine of dental hygiene.

According to a preferred embodiment thereof, the present invention also provides a biologically active hydroxyapatite compound capable of effectively exploiting also an antibacterial effect and, accordingly, effectively treating teeth and gums disorders and in general increasing oral hygiene even in the limited time available during the normal routine of dental hygiene.

According to this preferred embodiment, the nanoparticles further comprise an effective amount of an antibacterial ion.

More preferably, the nanoparticles of the invention comprise from 0.1% to 20% by weight with respect of the total Ca content of an antibacterial metal M ion substituted into the hydroxyapatite structure.

In this way, the antibacterial effect of the metal M ion may advantageously be optimized.

Preferably, the antibacterial metal M is selected from the group comprising Zn, Cu, Ag, and mixtures thereof.

Most advantageously, the aforementioned metal ions effectively exploit an antibacterial activity capable of preventing generation of carious tooth and periodontal diseases such as alveolar blennorrhoea and reducing halitosis phenomena.

Within the framework of this preferred embodiment, the nanoparticles have a molar ratio (Ca+M)/P greater than 1.7 and, more preferably, comprised between 1.7 and 1.8. In this way, it may be ensured that that the carbonate substitution in the hydroxyapatite structure has taken place mainly at site B, since a molar ratio (Ca+M)/P of non-substituted hydroxyapatites is of about 1.67.

Within the framework of this preferred embodiment, the nanoparticles of the invention can be represented for purely descriptive purposes by the following formula:

$$Ca_{10-x}M_x(PO_4)_{6-y}(CO_3)_{y+z}(OH)_{2-z}$$

wherein x is a number comprised between 0.0055 and 0.6, y is a number comprised between 0.065 and 0.9 and z is a number comprised between 0 and 0.32.

According to another aspect thereof, the present invention relates to a composition comprising the biologically active nanoparticles described herein.

In one preferred embodiment, such a composition is in a form suitable for oral hygiene and is advantageously capable of effectively improving teeth desensitization and remineralisation even in the limited time available during the normal routine of dental hygiene.

If the nanoparticles also include an antibacterial metal ion, the composition is also advantageously capable of effectively exploiting an antibacterial effect and, accordingly, effectively treating teeth and gums disorders and in general increasing oral hygiene even in the limited time available during the normal routine of dental hygiene.

In particular, it has been observed that the antibacterial effect of the metal ions may be directly obtained in situ at the dentine and enamel surface during the resolubilization of the nanoparticles deposited thereon, thus achieving a prolonged release of metal ions, even after dentifrice removal.

For the purposes of the invention, the composition including the nanoparticles of the invention may be in any physical form suitable for oral hygiene such as suspension, oil, gel or other solid product.

According to a preferred embodiment of the invention, the composition is in the form of a suspension including from 1% to 40% by weight, more preferably from 10% to 20% by weight, of biologically active nanoparticles.

Most advantageously, this suspension may be produced by means of a quite simple and economic method, as will be described in more detail hereinbelow, and may be directly used, for example as a gargle or mouthwash, to treat the teeth and gums or may be mixed with other ingredients when formulating a solid or liquid product such as a toothpaste or a mouthwash.

In a preferred embodiment of the invention, the suspension has pH comprised between 7 and 8 and, more preferably between 7 and 7.4.

In this way, the suspension may be advantageously directly used as such or mixed with other ingredients in the formulation of effective oral hygiene compositions.

In either case and in a preferred embodiment, it has proved advantageous to add suitable preserving agents, such as parabens or other orally acceptable preservatives known to those in the art, in order to prolong the shelf-life of the suspension and avoid the possibility of mold or bacterial contamination.

The inventors have surprisingly observed that the suspension of the invention is stable for an extended period of time even if no stabilizing agents are added thereto.

In particular, it has been observed that the suspension of the invention is stable for at least 30 days and, more generally, for about two-three months, without using any stabilizing agent.

According to an alternative preferred embodiment of the invention, the composition may be in the form of toothpaste, tooth powder, chewing gum for oral and dental hygiene, ointment for the gums, mouthwash and mouth bath concentrate and gargle. According to a preferred embodiment of the invention, the composition may comprise a combination of biologically active nanoparticles comprising an effective amount of an antibacterial ion and biologically active nanoparticles without said ion.

In this way, the entity of the antibacterial effect of the metal ion carried out at the dentine and enamel surface may be adjusted according to the most varied requirements. According to another preferred embodiment, in the oral composition of the invention the amount of biologically active nanoparticles will generally range from 3% to 30% by weight of the composition.

If the oral composition comprises a combination of biologically active nanoparticles comprising an effective amount of an antibacterial ion and biologically active nanoparticles without said ion, the amount of each of these two kinds of nanoparticles will generally range from 1.5% to 15% by weight of the composition.

The oral compositions of this invention will, of course, also contain other ingredients commonly used and known in the art to formulate such products, depending on the form of the oral product.

For instance, in the case of an oral product in the form of a dentifrice cream or paste, the product will preferably comprise a particulate abrasive agent, a humectant-containing liquid phase and a binder or thickener which acts to maintain the abrasive agent in stable suspension in the liquid phase. A surfactant and a flavoring agent are also usual preferred ingredients of commercially acceptable dentifrices.

For the purposes of the invention, a suitable particulate abrasive agent may be selected from the group comprising: silica, alumina, hydrated alumina, calcium carbonate, anhydrous dicalcium phosphate, dicalcium phosphate dihydrate and water-insoluble sodium metaphosphate. The amount of particulate abrasive agent will generally range from 0.5% to 40% by weight of the toothpaste.

Humectants commonly used are glycerol and sorbitol syrup (usually comprising an approximately 70% solution). However, other humectants are known to those in the art including propylene glycol, lactitol, and hydrogenated corn syrup. The amount of humectant will generally range from 10% to 85% by weight of the toothpaste. The liquid phase can be aqueous or nonaqueous.

Likewise, numerous binding or thickening agents have been indicated for use in dentifrices, preferred ones being sodium carboxymethylcellulose and xanthan gum. Others include natural gum binders such as gum tragacanth, gum karaya and gum arabic, alginates and carrageenans. Silica thickening agents include the silica aerogels and various precipitated silicas. Mixtures of binders may be used. The amount of binder included in a dentifrice is generally between 0.1% and 5% by weight.

It is usual to include a surfactant in a dentifrice and again the literature discloses a wide variety of suitable materials. Surfactants which have found wide use in practice are sodium lauryl sulfate and sodium lauroylsarcosinate. Other anionic surfactants may be used as well as other types such cationic, amphoteric and non-ionic surfactants. Surfactants are usually present in an amount comprised between 0.5% and 5% by weight of the dentifrice.

Flavors that are usually used in dentifrices are those based on oils of spearmint and peppermint. Examples of other flavoring materials used are menthol, clove, wintergreen, eucalyptus and aniseed. An amount comprised between 0.1% and 5% by weight is a suitable amount of flavor to incorporate in a dentifrice.

The oral composition of the invention may include a wide variety of other optional ingredients.

In the case of an oral product in the form of a toothpaste, these optional ingredients may include an anti-plaque agent such as moss extract, an anti-tartar ingredient, such as a condensed phosphate, e.g. an alkali metal pyrophosphate, hexametaphosphate or polyphosphate; a sweetening agent, such as saccharine and salts thereof; an opacifying agent, such as titanium dioxide; a preservative, such as formalin; a coloring agent; a pH controlling agent, such as an acid, base or buffer, such as citric acid. Suitable amounts of these optional ingredients may be easily selectable by those skilled in the art as a function of the specific characteristics to be imparted to the toothpaste.

In the case of an oral product in the form of a chewing gum, the composition will comprise in addition to the ingredients mentioned above a suitable gum base which may be easily selectable by those skilled in the art.

In the case of an oral product in the form of a mouthwash or gargle, the composition will comprise suitable ingredients in liquid or soluble form easily selectable by those skilled in the art, such as sorbitol, glycerol, oils and flavoring materials, solubilizing agents such as hydrogenated and ethoxylated ricin oil, surfactants, such as sodium lauryl sulfate and sodium lauroylsarcosinate, preserving agents, viscosity regulators and other suitable ingredients which may be easily selectable by those skilled in the art.

For a fuller discussion of the formulation of oral compositions reference is made to Harry's Cosmeticology, Seventh Edition, 1982, Edited by J. B. Wilkinson and R. J. Moore.

According to another aspect thereof, the present invention relates to an improved process for producing an aqueous suspension including a biologically active hydroxyapatite compound which requires low investment and operating costs.

A process for preparing an aqueous suspension including biologically active nanoparticles of a carbonate-substituted hydroxyapatite according to the invention is defined in attached claim 20.

More specifically, the process of the invention comprises the steps of:
- a) preparing an aqueous solution or suspension comprising a Ca compound;
- b) forming nanoparticles of a carbonate-substituted hydroxyapatite by adding $PO_4^{3-}$ ions to the aqueous solution or suspension of step a) while simultaneously agitating the same over a time comprised between 30 minutes and 8 hours while maintaining said solution or suspension at a temperature lower than or equal to 60° C.;
- c) agitating the suspension obtained from step b) over a time of at least two hours at a temperature lower than or equal to 60° C.

Most advantageously, this process allows to prepare in a fairly quick and economical way a suspension of biologically active nanoparticles which may be readily used as such as a composition for oral hygiene or used in admixture with other ingredients to yield compositions for oral hygiene.

Most advantageously, furthermore, this process allows to prepare a suspension of biologically active nanoparticles which is stable for an extended period of time even if no stabilizing agents are added thereto.

As indicated above, it has been observed that the suspension thus prepared is stable for at least 30 days and, more generally, for about two-three months, without using any stabilizing agent.

For the purposes of the invention, the aforementioned step a) of preparing an aqueous solution or suspension comprising a Ca compound may be carried out in any conventional manner, such as by dissolving or suspending the Ca compound in water. According to a preferred embodiment of the invention, the Ca compound is a calcium salt selected from the group comprising: calcium hydroxide, calcium carbonate, calcium acetate, calcium oxalate, calcium nitrate, and mixtures thereof.

In this way, the cost of the process may advantageously be reduced since these Ca compounds are commodities readily available from the marked at a very low cost. Additionally, these Ca compounds are easily workable and stockable to the advantage of the manufacturing operations.

In the process of the invention, step a) is preferably carried out in order to achieve a suspension of nanoparticles having a basic pH. Preferably, the aqueous solution or suspension of step a) has a pH comprised between 8 and 12.

According to a preferred embodiment of the invention, the aforementioned step a) is carried out in substantial absence of orally non-acceptable anions.

In this way, a suspension of nanoparticles may be produced which does not require any additional treatment to remove undesired substances and which may directly used as such, save for an optional pH adjustment by means of a suitable agent, such as citric acid.

In the process of the invention, the nanoparticles of carbonate-substituted hydroxyapatite are formed in step b) by adding $PO_4^{3-}$ ions to the aqueous solution or suspension of step a) and by simultaneously agitating this solution or suspension in order to capture the carbon dioxide present in the atmosphere and achieve the desired carbonate substitution at the phosphate site (B) of the hydroxyapatite compound being formed.

In this way, the carbonate substitution may be advantageously carried out by simply agitating the solution or suspension for example by means of a mechanical stirrer. In an alternative embodiment, the required agitation of the solution or suspension may be achieved by bubbling air, a $CO_2$-containing gas or a mixture thereof into the liquid phase or by combining a mechanical stirring with a gas bubbling.

For the purposes of the invention, the $PO_4^{3-}$ ions are added to the aqueous solution or suspension of step a) over a time which generally depends on the amount of the used phosphoric solution with respect to the amount of the basic, calcium solution or suspension, and which may be selected by those skilled in the art.

Preferably, step b) is carried out over a time comprised between 30 minutes and 2 hours in order to keep the reaction time and the operating costs as low as possible.

According to the invention, step b) is carried out while maintaining said solution or suspension at a temperature lower than or equal to 60° C.

The inventors have observed that in this way the crystallinity degree CD of the nanoparticles may be kept below the aforementioned maximum value of 40% (70% in the case of CD').

In a preferred embodiment of the invention, step b) is carried out while maintaining said solution or suspension at a temperature lower than or equal to 40° C. and more preferably comprised between 25° and 40° C.

In this way, the crystallinity degree CD of the nanoparticles may be kept within the aforementioned preferred range of values (CD=25-35%; CD'=40-60%).

According to a preferred embodiment of the invention, step b) is carried out by adding, preferably dropwise, an aqueous solution including $PO_4^{3-}$ ions to the aqueous solution or suspension of step a).

According to an alternative preferred embodiment of the invention, the aqueous solution including $PO_4^{3-}$ ions added in step b) may further comprise $HCO_3^-$ ions.

In this way, it may be possible to adjust to the proper extent the desired carbonate substitution at the phosphate site (B) of the hydroxyapatite compound being formed. Within the framework of this preferred embodiment, the aforementioned aqueous solution including $HCO_3^-$ and $PO_4^{3-}$ ions may be prepared by bubbling air, $CO_2$ or a mixture thereof through water to obtain a solution of carbonic acid and then adding $H_3PO_4$ thereto.

According to another alternative preferred embodiment of the invention, step b) may be carried out by simultaneously adding a first solution containing $CO_3^{2-}$ ions and a second solution containing $PO_4^{3-}$ ions to the aqueous solution or suspension of step a).

In a preferred embodiment of the invention, the process is carried out such that the suspension of nanoparticles obtained from step c) has a pH comprised between 7 and 8 and, more preferably, between 7 and 7.4.

In this way and as already outlined above, the process of the invention allows to produce a suspension which may be advantageously directly used as such or mixed with other ingredients in the formulation of effective oral hygiene compositions with a remarkable simplification of the manufacturing operations of the compositions and a remarkable cost reduction.

As noted above, the suspension of nanoparticles produced in this way also shows remarkable stability characteristics and has a shelf life of at least 30 days and, more generally, of about two-three months, even if no stabilizing agents are added thereto. According to a preferred embodiment of the invention, the aqueous solution or suspension of step a) may further comprise an oxide or a salt of an antibacterial metal M.

Preferably, the antibacterial metal M is selected from the group comprising Zn, Cu, Ag, and mixtures thereof.

In this way, a suspension of nanoparticles may be produced which also exhibit an antibacterial effect enhancing the oral hygiene characteristics of the suspension or of the other products (liquid or solid) in which the suspension is incorporated.

In a preferred embodiment, the aforementioned metal salt is an orally acceptable organic or inorganic salt selected from the group comprising: lactates, gluconates, citrates, acetates and hydroxides.

In this way, a suspension of nanoparticles may be produced which does not require any additional treatment to remove undesired substances and which may directly used as indicated above.

In a preferred embodiment, step b) is carried out such that the ratio of the Ca and M ions contained in the solution or suspension of step a) and the $PO_4^{3-}$ ions added thereto is greater than 1.7.

In this way, it may be ensured that that the carbonate substitution in the hydroxyapatite structure has taken place mainly at phosphate site B and a suspension of nanoparticles may be produced which advantageously exploits an antibacterial activity capable of preventing generation of carious tooth and periodontal diseases such as alveolar blennorrhoea and reducing halitosis phenomena.

In the process of the invention, the growth of the nanoparticles of a carbonate-substituted hydroxyapatite is accomplished in step c) by agitating the suspension obtained from step b) (during which mainly a nucleation of the nanoparticles is taking place) over a time of at least two hours at a temperature lower than or equal to 60° C. Preferably, step c) is carried out over a time comprised between 2 and 24 hours and more preferably between 2 and 12 hours, as required by the circumstances in order to have a growing time of the nanoparticles sufficient to reach the desired size and in order to obtain a single phase.

In a preferred embodiment of the invention, step c) is carried out while maintaining the suspension of nanoparticles at a temperature comprised between 25° and 40° C.

In a preferred embodiment of the invention, step c) is carried out while maintaining the suspension of nanoparticles at the same temperature of step b).

In this way, the process may be advantageously carried out with a simpler control and at a lower cost.

According to another aspect thereof, the present invention relates to an improved process for preparing a biologically active hydroxyapatite compound which requires low investment and operating costs.

A process for preparing biologically active nanoparticles of a carbonate-substituted hydroxyapatite according to the invention is defined in attached claim 35.

More specifically, the process of the invention comprises the steps of:
a) preparing an aqueous suspension including said nanoparticles by means of a process as herein described;
b) separating solid nanoparticles from the suspension obtained from step a);
c) drying the wet solid nanoparticles thus obtained.

In a preferred embodiment, the separation step b) is carried out by decantation, centrifugation or filtration using apparatuses and techniques well known to those skilled in the art.

In a preferred embodiment, the drying step c) is carried out by freezing the wet solid nanoparticles at a temperature lower than 0° C. until reaching a constant weight.

Within the framework of this preferred embodiment, the drying step c) is preferably carried out by freeze-drying the wet solid nanoparticles at a temperature comprised between −20° and −50° C., most preferably at about −40° C.

In a preferred embodiment, the process may also comprise the additional step d) of washing the separated solid nanoparticles with water or a basic solution prior to effecting the drying step c).

Advantageously, this additional washing step d) serves the useful function of removing any acid residues possibly absorbed or trapped by the nanoparticles.

According to another aspect thereof, the present invention relates to an improved process for manufacturing a toothpaste comprising a biologically active hydroxyapatite compound which requires low investment and operating costs.

A first process for manufacturing a toothpaste comprising biologically active nanoparticles of a carbonate-substituted hydroxyapatite according to the invention is defined in attached claim 39 and comprises the steps of:
a) preparing an aqueous suspension including said nanoparticles by means of a process as herein described;
b) mixing said aqueous suspension with other ingredients of the toothpaste.

As already noted above, this process advantageously allows to readily incorporate the nanoparticles in the toothpaste in a quite simple and convenient manner exploiting the useful properties, in particular stability and pH characteristics, of the suspension of nanoparticles produced in accordance with the invention.

Quite advantageously, the process for manufacturing a toothpaste of the invention does not require any separation or drying of the nanoparticles, with a notable reduction of the manufacturing plant complexity, of the related investment and operating costs, of product losses during the manufacture and of production rejects.

In addition, the mixing step of the aqueous suspension of nanoparticles with other ingredients of the toothpaste may be carried out with a better temperature control since the aqueous suspension reduces the friction and helps in removing the heat generated in the mixing apparatus.

An alternative second process for manufacturing a toothpaste comprising biologically active nanoparticles of a carbonate-substituted hydroxyapatite according to the invention is defined in attached claim 40 and comprises the steps of:
a) preparing solid nanoparticles by means of a process as herein described;

b) mixing the solid nanoparticles with other ingredients of the toothpaste.

This alternative process allows to manufacture a toothpaste in all those instances in which the use of the above-described suspension of nanoparticles may not be desirable for logistic or other reasons.

In a preferred embodiment of the manufacturing processes described above, the mixing step b) is carried out in a mixing apparatus maintained under a predetermined vacuum degree, easily selectable by those skilled in the art in order to obtain a uniform mixture of ingredients, reached by using conventional vacuum pumps.

In a preferred embodiment of the first manufacturing process, the mixing step b) is carried out by b1) mixing the aqueous suspension of step a) with other ingredients of the toothpaste except for any surfactant;
b2) incorporating at least one surfactant into the mixture thus obtained.

In this way, the formation of foam during the mixing operation may be minimized. Within the framework of this embodiment, the incorporation step b2) is preferably carried out under vacuum using a conventional equipment in order to minimize the undesired formation of foam.

According to another aspect thereof, the present invention relates to a method of locally remineralising the teeth comprising contacting the teeth with a composition comprising biologically active nanoparticles as described herein.

Most advantageously and thanks to the characteristics of the nanoparticles described above, such a method allows to effectively remineralise the teeth even in the limited time available during the normal routine of dental hygiene.

The contacting step of the remineralising method may be carried out in a number of ways depending upon the form of the nanoparticles-containing composition. For example, if the composition is a toothpaste, the contacting step may be simply carried out by washing the teeth, while if the composition is a mouthwash, the contacting step is carried out by maintaining the mouthwash in the oral cavity for a suitable time, for example few minutes.

According to the invention and as will be shown in greater detail below, in fact, the nanoparticles of the invention possess such a high remineralising activity that its effect may be detected even by contacting the nanoparticles with the teeth for a limited period of time.

BRIEF DESCRIPTION OF THE DRAWINGS

Additional features and advantages of the present invention will be more readily apparent by the following Examples of some preferred embodiments of the various aspects of the present invention given hereinbelow by way of illustration and not of limitation, which aspects will be better understood with reference to the attached drawings.

In these drawings.

Figure 1:
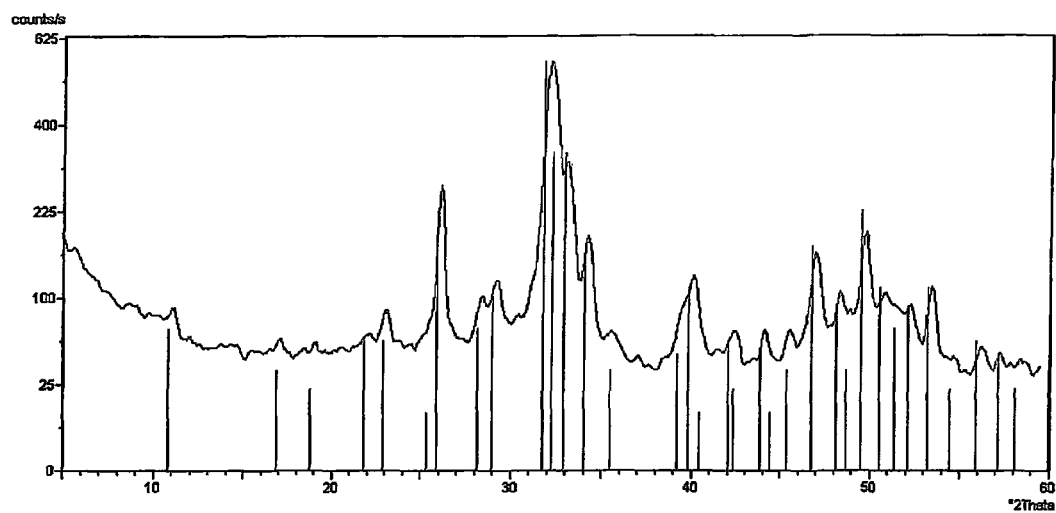
FIG. 1 shows an X-Ray diffraction pattern of one example of biologically active nanoparticles according to the invention.

In the following Examples, percentages and parts are by weight unless otherwise indicated.

EXAMPLE 1

Preparation of an Aqueous Suspension of Nanoparticles 2184 g of an aqueous suspension of biologically active nanoparticles according to the invention was prepared according to the following method.

In a first step, an aqueous suspension comprising 356.2 g of $Ca(OH)_2$, 48.8 g of ZnO and 45 g of $Ca(CO_3)$ in 1060 g of $H_2O$ was prepared in a conventional reaction vessel while agitating the ingredients with a mechanical stirrer.

During this step, the resulting suspension was brought to a temperature of 40°±2° C. by means of an electrical resistance or by any other suitable heating element such as for example a thermostated jacket in which a heating fluid, such as oil or vapor, is circulated.

Once the desired temperature was reached, nanoparticles of a carbonate-substituted hydroxyapatite were formed by adding dropwise $PO_4^{3-}$ ions to the aqueous suspension of the preceding step while simultaneously agitating the same. In this case, 674 g of an acid solution constituted by a mixture 70/30 of $H_3PO_4(75\%)/H_2O$, were added with a dripping speed of 22 g·min$^{-1}$ (0.4 g·sec$^{-1}$), while continuously stirring and maintaining constant the temperature of the reaction vessel.

After about 30' and 30" a suspension of nanoparticles was obtained which was subsequently agitated over a period of time of about two hours at a temperature of 40°±2° C., after which a suspension having a total content of about 30-31% by weight of nanoparticles and having a pH of about 7±0.2 was obtained.

The suspension of nanoparticles was readily useable as such or as an active ingredient for the subsequent preparation of a toothpaste, mouthwash or other oral or dental composition according to the invention.

EXAMPLE 2

Preparation of Solid Nanoparticles 670 g of biologically active nanoparticles according to the invention were prepared by first preparing 2184 g of an aqueous suspension according to the method and using the same ingredients of preceding Example 1 and then by carrying out the following additional steps.

Firstly, the solid nanoparticles were separated from the liquid by filtering on a Millipore paper with a pore diameter of 45 μm and then were repeatedly washed with a diluted water solution of $CaCO_3$ to remove any acid residues.

The wet solid nanoparticles thus obtained were then freeze-dried at −40° C. until they reached a constant weight, sieved at (0=120-20 microns) and stored at a temperature of 0-4° C.

The nanoparticles thus obtained, which had the aspect of a white powder, were then characterized as follows.
1) X-Ray Diffraction (XRD)

X-ray powder patterns were collected using a Philips PW 1710 powder diffractometer equipped with a secondary graphite monochromator using Cu Kα radiation generated at 40 kV and 40 mA. The instrument was configured with a 1° divergence and 0.2 mm receiving slits. The samples were prepared using the front loading of standard aluminium sample holders which are 1 mm deep, 20 mm high and 15 mm wide. The 2θ range was from 5° to 60° with a step size (2θ) of 0.05° and a counting time (s) of 3.

In FIG. 1 the XRD pattern of the nanoparticles, which allows to determine the crystallinity degree of the nanoparticles, is shown.

In FIG. 1, the line intensity is related to its intensity percentage (arbitrary units), considering the highest line equal to 100.

The crystallinity degree, was evaluated according to the aforementioned Landi et al. method and Erkmen method.

According to the Landi et al. method, the crystallinity degree of the nanoparticles evaluated from the XRD pattern reported in FIG. 1 was of about 30%.

According to the Erkmen method, the crystallinity degree of the nanoparticles evaluated from the XRD pattern reported in FIG. 1 was of about 52%.

Figure 2:
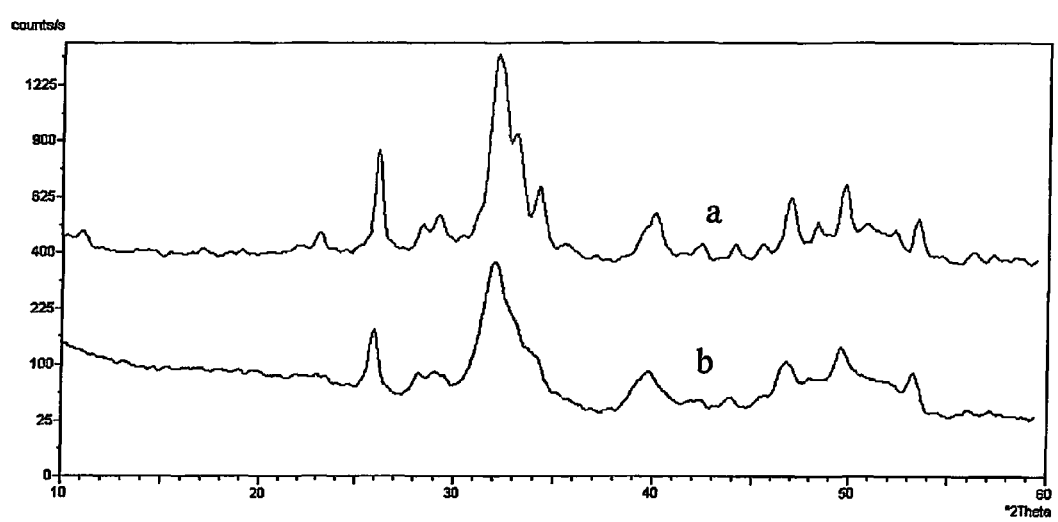
FIG. 2 shows the X-Ray diffraction patterns of one example of biologically active nanoparticles according to the invention (a) and of natural (dentine) apatite nanoparticles (b)
Figure 3A:
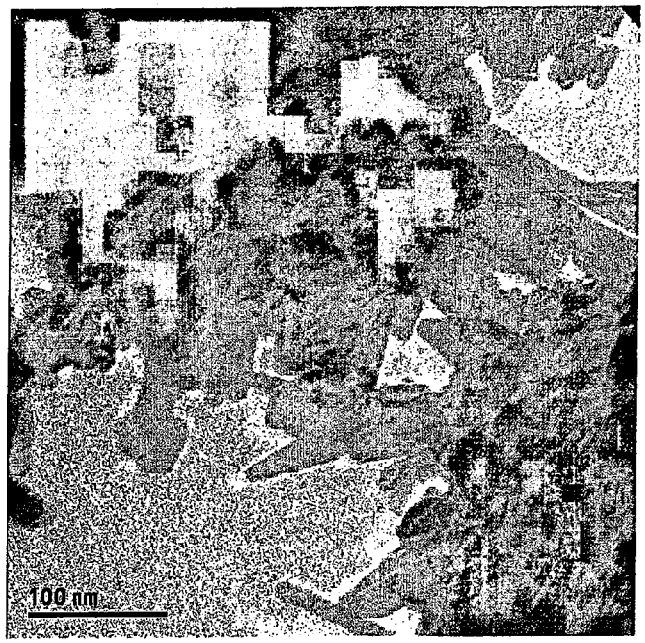
FIGS. 3a, 3b, 3c and 3d show TEM images of some examples of biologically active nanoparticles according to the invention which display the nanometric size of the particles.
Figure 3B:
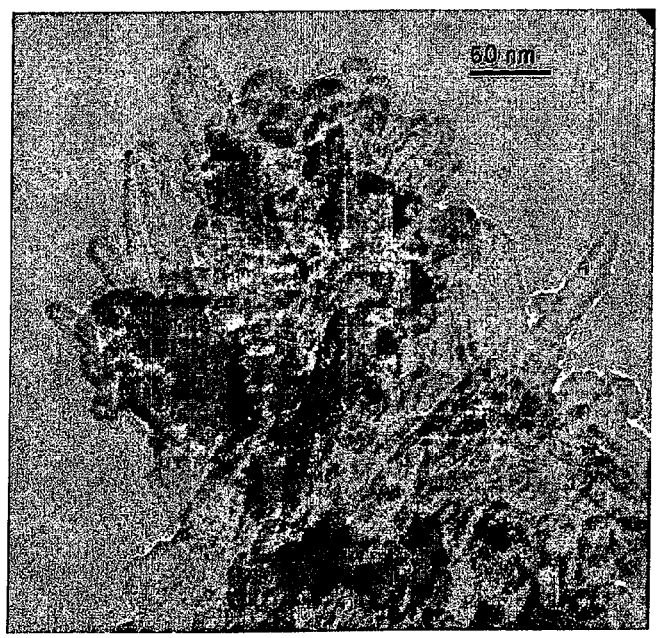
Figure 3C:
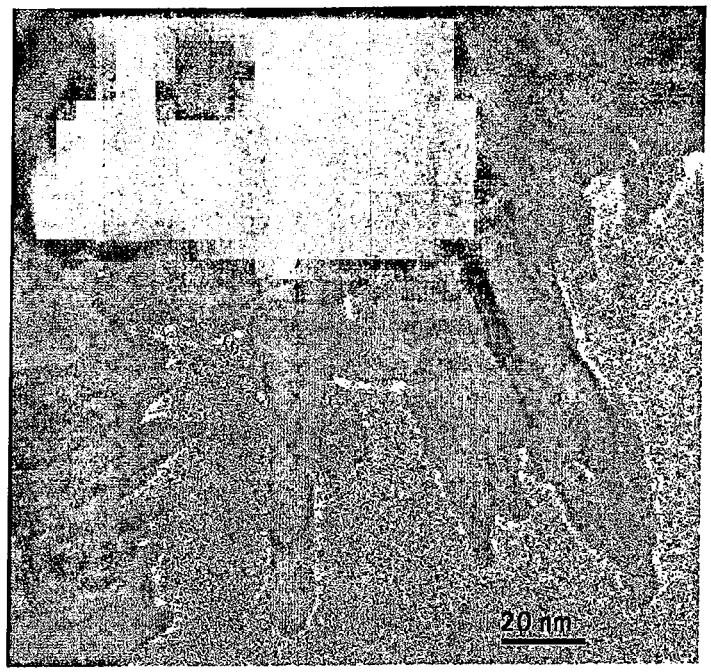
Figure 3D:
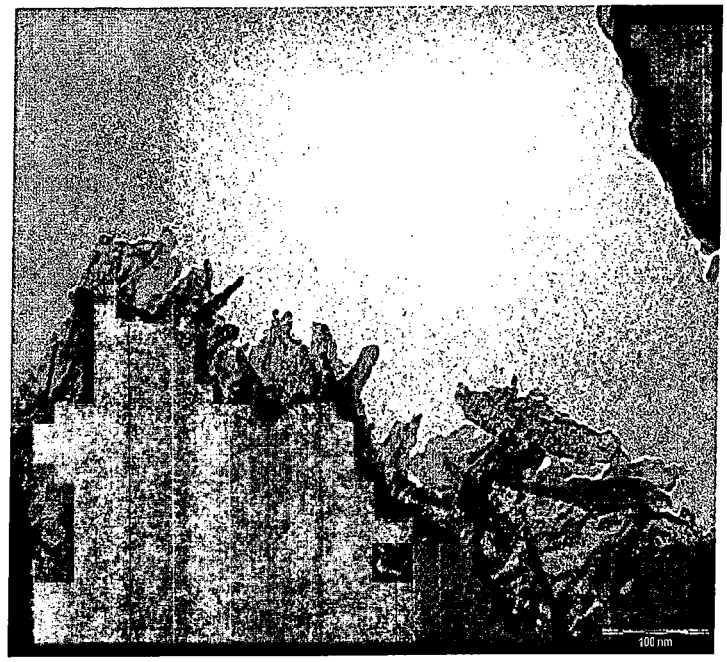

As to nature of the carbonate-substituted hydroxyapatite nanoparticles and as may also be gathered from the patterns reported in FIG. 2, in which curve a is the pattern of the biologically active hydroxyapatite nanoparticles according to the invention and curve b is the pattern of natural hydroxyapatite nanoparticles, it may be observed the similarity between natural (dentine) hydroxyapatite nanoparticles and the hydroxyapatite nanoparticles according to the invention.

2) Morphological Characterisation by Transmission Electron Microscopy (TEM)

Transmission Electron Microscopy (TEM) observations were carried out using a Philips CM 100. The powdered samples were ultrasonically dispersed in ultrapure water and then a few droplets were dropped on holey-carbon foils supported on conventional copper microgrids. TEM images of the biologically active nanoparticles according to the invention are reported in FIGS. 3a, 3b, 3c and 3d respectively where it is possible to appreciate the elongate shape of the nanoparticles with acicular and platelet shape morphology very close to those observed for bone apatite crystals. The nanoparticles had an average length L of about 100 nm, an average width W of about 10 nm and an average thickness T of about 5 nm.

The average aspect ration A/R was 10.

3) Thermal Analysis (TGA-DSC)

Thermogravimetric investigations were carried out on the nanoparticles using a Thermal Analysis SDT Q 600. Heating was performed in nitrogen flow (100 ml/min) using an alumina sample holder at a rate of 10° C./min up to 1000° C. The weight of the samples was around 10 mg.

Figure 4:
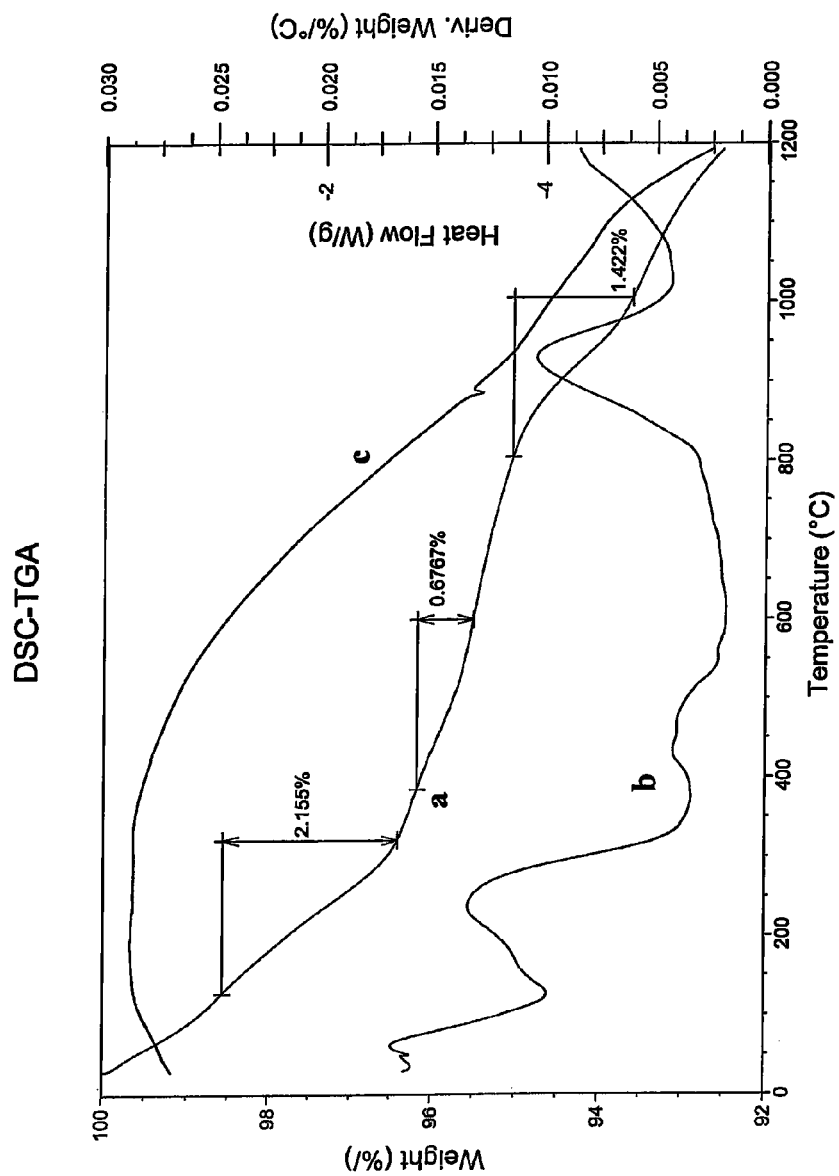
FIG. 4 shows a thermogravimetric plot of one example of biologically active nanoparticles according to the invention.

FIG. 4 reports the results of a thermogravimetric analysis of the nanoparticles showing the weight decreases relating to the decomposition of the inorganic phase. Line a corresponds to percentage weight loss as a function of the treatment temperature and line b represents the derivative of the percentage weight loss respect to the temperature.

Line c corresponds to heat flow involved into the phases transitions which are not present in the samples of the nanoparticles.

Line b shows a broad peak between 150° C. and 300° C. due to the loss of the physically absorbed water (weight loss of 2.2±0.5%), a broad peak between 400° C. and 600° C. due both to the loss of the chemically absorbed water and to the decarbonation process (weight loss of 0.7±0.3%). The peak between 800° C. and 1000° C. can be attributed to the dehydroxylation process (weight loss of 1.5±0.5%). The peak broadness is partially due to the low crystallinity degree of the nanoparticles.

4) Surface Area Analysis (BET)

The specific surface area of the nanoparticles was evaluated by the Brunauer, Emmet, Teller method [S. Brunauer, P. H. Emmet, E. Teller, *Adsorption of gases in multimolecular layers. J. Am. Chem. Soc.* 60 (1938) 309-319], [S. J; Greg, K. S. Sing (Eds.), *Adsorption, Surface Area and Porosity, Academic Press,* 1997 O. Gauthir, J. M. Boiler, E. Aguado, P. Piletand, G. Daculsi] carried out by means of a Carlo-Erba Sorpty 1750 instrument and using $N_2$ as adsorption gas.

Analyses were performed on 300 mg of samples. Before gas absorption, the samples were dried under vacuum (2 mbar) while increasing the temperature, at a speed of 10° C./min, from 25° C. to 100° C. $N_2$ adsorption was then carried out keeping the sample in liquid $N_2$. Each surface area measurement supplied by the instrument corresponds to the mean of three values.

The average surface area of the nanoparticles was of about 30 $m^2/g$.

5) Chemical Composition: Inductively Coupled Plasma-Optical Emission Spectrometry (ICP-OES) analysis The amount of calcium, zinc and phosphorous in the samples of nanoparticles was obtained using and Inductively Coupled Plasma-Optical Emission Spectrometry (ICP-OES) technique. The ICP-OES measurements were carried out with a Perkin Elmer Optima 4200 DV instrument. The samples had been previously dissolved in ultrapure nitric acid 1% to obtain a concentration of the elements between 1 and 8 ppm.

The nanoparticles exhibited a bulk (Ca+M)/P molar ratio of about 1.98 and a Zinc content of about 18% by weight with respect of the total Ca content.

6) Spectroscopic Characterization by Fourier Transform Infrared (FTIR) Analysis

The infrared spectra were registered from 4000 to 400 $cm^{-1}$ at 2 $cm^{-1}$ resolution by using a Bruker IFS 66v/S spectrometer. Pellets (KBr) were obtained under vacuum by using powdered samples (1 mg) carefully mixed with infrared grade KBr (200 mg).

Figure 5:
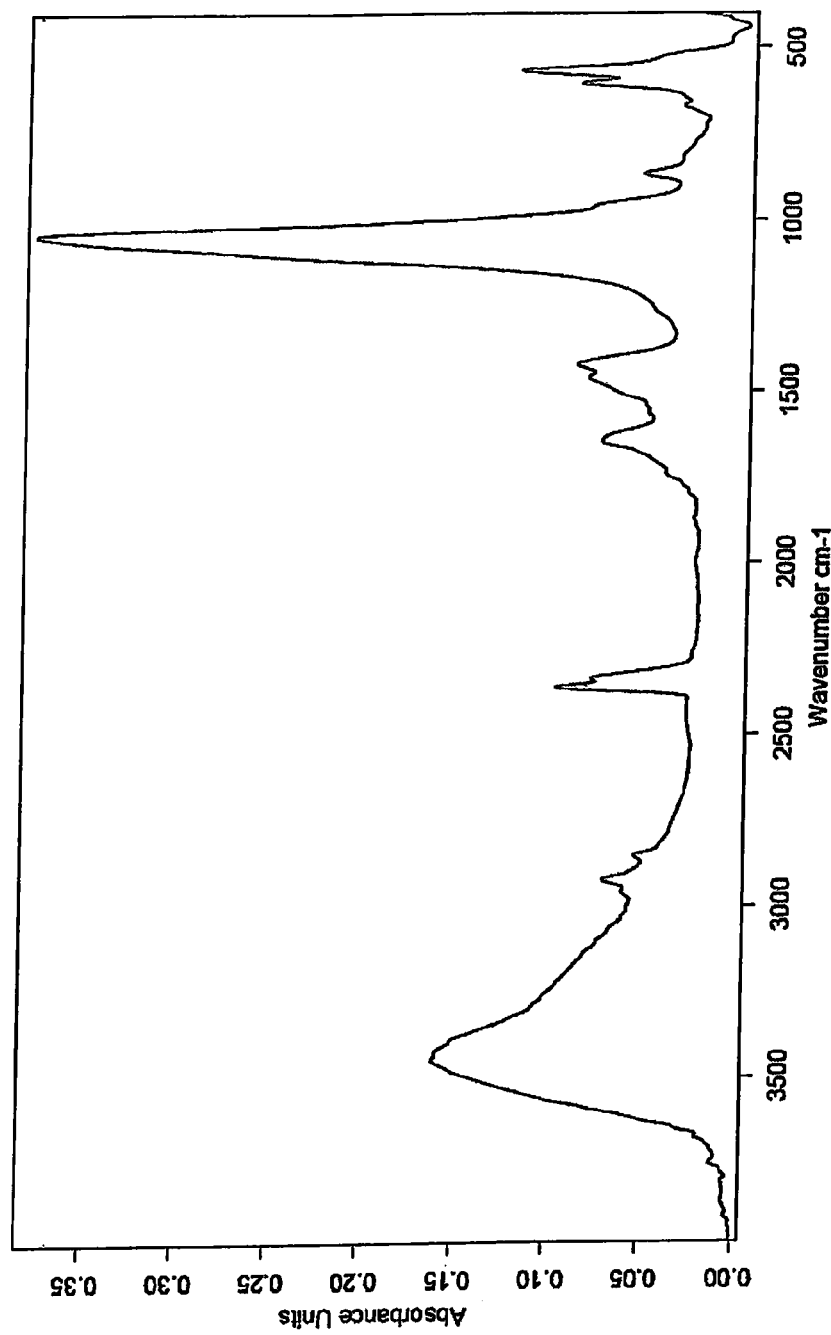
FIG. 5 shows a FTIR spectrum of one example of biologically active nanoparticles according to the invention.

The FTIR spectrum of the nanoparticles is shown in FIG. 5. The spectrum shows the signals related to the groups $PO_4^{3-}$ (1037 $cm^{-1}$), $HPO_4^{2-}$ (955 $cm^{-1}$), Off (3444 $cm^{-1}$ and 1630 $cm^{-1}$), $CO_3^{2-}$ (870 $cm^{-1}$). A comparison between the peak area at 870 $cm^{-1}$ of the nanoparticles and the peak area at 870 $cm^{-1}$ of a $CaCO_3$ reference standard allowed to evaluate a $CO_3^{2-}$ amount of about 3% by weight based on the total weight of the nanoparticles.

The band at 870 $cm^{-1}$ provides information about the apatite carbonation type. The deconvolution profile of the carbonate peak at 870 $cm^{-1}$ allows to deduce that the hydroxyapatite carbonation is predominantly of type B (A/B ratio of approximately 0.05).

The relevant characterization data of the nanoparticles are summarized in the following Table 1.

EXAMPLE 3

2124 g of biologically active nanoparticles according to the invention were prepared by first preparing 1449.5 g of an aqueous suspension according to the method and using the same ingredients of preceding Example 1 save for the fact that the amount of water was of about 1000 g, the amount of ZnO was of 4.5 g, the amount of $CaCO_3$ was of 22.5 g, the amount of $Ca(OH)_2$ was 422.5 g.

During this step, the resulting suspension was brought to a temperature of 40°±2° C. by the same method of the preceding Example 1.

Once the desired temperature was reached, nanoparticles of a carbonate-substituted hydroxyapatite were formed by adding dropwise $PO_4^{3-}$ ions in the same way and in the same amounts as described in preceding Example 1.

After about 30' and 30" a suspension of nanoparticles was obtained which was subsequently treated in the same manner described in preceding Example 1.

The nanoparticles were then separated from the aqueous suspension thus obtained according to the separation method described in the preceding Example 2.

The nanoparticles thus obtained were then characterized according to the procedures and methods described in Example 2. The relevant characterization data of the nanoparticles are reported in the following Table 1.

EXAMPLE 4

2184 g of biologically active nanoparticles according to the invention were prepared by first preparing 1510 g of an aqueous suspension according to the method and using the same ingredients of preceding Example 1 save for the fact that the amount of $Ca(OH)_2$ was of about 405 g and that no metal ion ingredient was added to the suspension. During this step, the resulting suspension was brought to a temperature of 40°±2° C. by the same method of the preceding Example 1.

Once the desired temperature was reached, nanoparticles of a carbonate-substituted hydroxyapatite were formed by adding dropwise $PO_4^{3-}$ ions in the same way and in the same amounts as described in preceding Example 1.

After about 30' and 30" a suspension of nanoparticles was obtained which was subsequently treated in the same manner described in preceding Example 1.

The nanoparticles were then separated from the aqueous suspension thus obtained according to the separation method described in the preceding Example 2.

The nanoparticles thus obtained were then characterized according to the procedures and methods described in Example 2. The relevant characterization data of the nanoparticles are reported in the following Table 1.

TABLE 1

| Parameter | Example 2 | Example 3 | Example 4 |
|---|---|---|---|
| Crystallinity degree CD [%] | 30 | 35 | 30 |
| Crystallinity degree CD' [%] | 52 | 60 | 60 |
| Length L [nm] | 100 | 150 | 150 |
| Width W [nm] | 10 | 20 | 15 |
| Aspect Ratio AR | 10 | 7.5 | 10 |
| Thickness T [nm] | 5 | 5 | 10 |
| Surface area [m²/g] | 30 | 40 | 30 |
| (Ca + M)/P molar ratio | 1.98 | 1.8 | 1.98*** |
| Metal content [wt %]* | 18 | 1.5 | 0 |
| $CO_3^{2-}$ content [wt %]** | 4% | 2% | 4% |
| A/B ratio | 0.05 | 0.1 | 0.05 |

*= % by weight with respect to the total Ca content.
**= % by weight with respect to the total weight of the nanoparticles.
***= in this case only Ca was present

EXAMPLE 5

Evaluation of the Teeth Remineralisation Activity of the Aqueous Suspension of Nanoparticles In order to evaluate the teeth remineralisation activity of the aqueous suspension of nanoparticles prepared in accordance with the preceding Example 1 the following test was carried out.

Fresh bovine teeth were obtained and a slab of radicular dentine was obtained by cutting the teeth with a diamond saw. The periodontal ligament was removed using a metal curette and the root cementum were removed using a diamond bur under water cooling. The dentine was etched with ortophosphoric acid for 1 minute in order to remove the smear layer and expose the dentinal tubules. The acid was washed away with a water spray for 1 minute and the specimens were left just wet.

Then an aliquot of the suspension of nanoparticles according to the preceding Example 1 was applied on the dentine slabs using a brush. The slabs were left wet in an incubation chamber at 37° C. for an application time of about 1 minute after which time the specimens were rinsed with air-water spray for 1 minute and processed for Scanning Electron Microscopy (SEM).

Figure 6A:
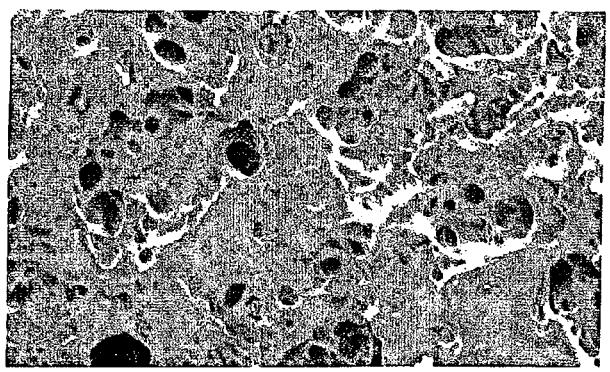
FIGS. 6a, 6b and 6c show respective SEM images of a slab radicular dentine of fresh bovine teeth in a demineralized condition (FIG. 6a), after a 1-minute contact (FIG. 6b) and after a 10-minutes contact (FIG. 6c) with a suspension of biologically active nanoparticles according to the invention.
Figure 6B:
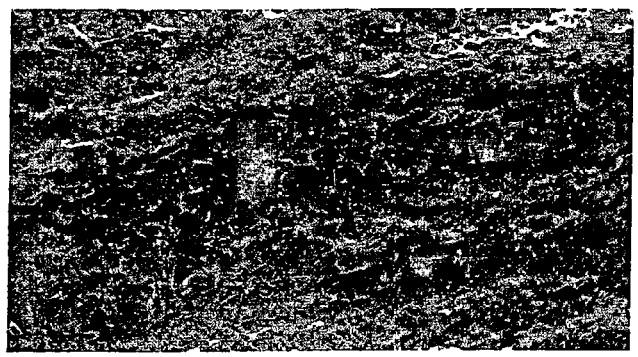
Figure 6C:
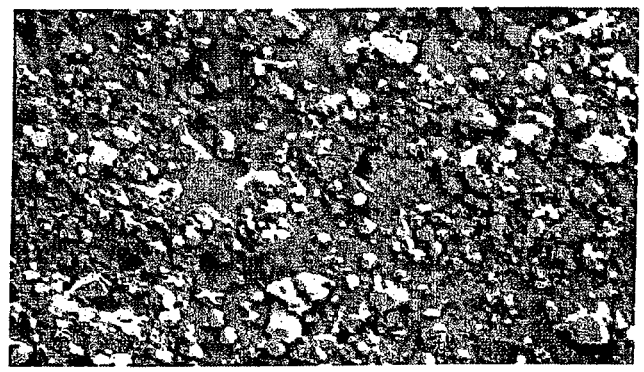

FIGS. 6a, 6b and 6c show the features of the dentine at baseline (FIG. 6a-demineralized) and of remineralised specimens after application of the nanoparticles for 1 minute (FIG. 6b) and for 10 minutes (FIG. 6c).

FIG. 6b shows a remarkable crystals formation and consequent obliteration of dentinal patent tubules even with a contact for a very limited time (1 minute) between the dentine and the suspension of nanoparticles. FIG. 6c shows an enhanced deposition of the nanoparticle on dentine substrate as a function of contact time.

EXAMPLE 6

Toothpaste

A toothpaste including biologically active nanoparticles according to the invention was prepared according to the following method and from the following ingredients. In a first step, an aqueous suspension including biologically active nanoparticles (total solid content: 30% by weight) was prepared in the same manner and using the same ingredients and quantities described in Example 1.

The aqueous suspension thus obtained, was then mixed with the other ingredients of the toothpaste as shown in the table below except for the surfactant.

The mixing was carried out in a conventional mixing apparatus maintained under a suitable vacuum degree selected among the usual values known to those skilled in the art.

Once a homogeneous mixture was obtained, the surfactant was incorporated in the mixing apparatus while maintaining a predetermined vacuum degree selected among the usual values known to those skilled in the art.

In this way, a toothpaste was obtained having the composition reported in the following Table 2.

TABLE 2

| Ingredient | Amount [%] |
|---|---|
| Sodium carboxymethylcellulose | 1.0 |
| HA-Zn nanoparticles* | 7.5 |
| HA nanoparticles** | 7.5 |
| Sorbitol syrup | 15.0 |
| Glycerine | 15.0 |
| Sodium saccharine | 0.25 |
| Hydroglycolic moss extract titrated in 2% usnic acid | 0.5 |
| Thickening silica | 1.0 |
| Abrasive silica | 18.0 |
| Tetrapotassium pyrophosphate | 3.0 |
| Titanium dioxide | 0.9 |
| Sodium lauryl sulfate | 0.5 |
| Mint flavor | 1.3 |

TABLE 2-continued

| Ingredient | Amount [%] |
| --- | --- |
| Citric acid | 0.25 |
| Water | balance |

*= Biologically active nanoparticles of a carbonate-substituted hydroxyapatite including Zn ions prepared in accordance with Example 1.
**= Biologically active nanoparticles of a carbonate-substituted hydroxyapatite prepared in accordance with the procedure of Example 1 except for the fact that no Zn ions were used.

EXAMPLE 7

Mouthwash

A mouthwash including biologically active nanoparticles according to the invention was prepared by mixing a suspension produced in accordance with the preceding Example 1 in a conventional way with conventional ingredients.

A mouthwash was obtained having the composition reported in the following Table 3.

TABLE 3

| Ingredient | Amount [%] |
| --- | --- |
| HA-Zn nanoparticles* | 2.5 |
| HA nanoparticles** | 2.5 |
| Sorbitol syrup | 3 |
| Glycerine | 3 |
| Sodium saccharine | 0.25 |
| Hydroglycolic moss extract titrated in 2% usnic acid | 0.5 |
| Tetrapotassium pyrophosphate | 1 |
| Sodium lauryl sulfate | 0.2 |
| Mint flavor | 0.5 |
| Citric acid | 0.1 |
| Water | balance |

EXAMPLE 8

Chewing Gum for Tooth Cleaning

A chewing gum including biologically active nanoparticles according to the invention was prepared by mixing solid dried nanoparticles produced in accordance with the preceding Example 2 in a conventional way with conventional ingredients.

A chewing gum was obtained having the composition reported in the following Table 4.

TABLE 4

| Ingredient | Amount [%] |
| --- | --- |
| Chewing gum base | 91.65 |
| HA-Zn nanoparticles* | 2 |
| HA nanoparticles** | 2 |
| Glycerine | 3 |
| Sodium saccharine | 0.025 |
| Hydroglycolic moss extract titrated in 2% usnic acid | 0.1 |
| Mint flavor | 1 |

What is claimed is:

1. Biologically active nanoparticles of a carbonate-substituted non-stoichiometric hydroxyapatite, having:
   a) a crystallinity degree CD lower than 40%, the crystallinity degree being defined as $CD = (1 - X/Y) 100$ wherein:
   Y=height of the diffraction maximum at $2\grave{e}=33°$, X=height of the diffraction background at $2\grave{e}=33°$ of the nanoparticles X-ray diffraction pattern;
   b) a length L ranging from 20 to 200 nm and a width W ranging from 5 to 30 nm; and
   c) an aspect ratio AR comprised between 2 and 40, the aspect ratio being defined as $AR = L/W$.

2. Biologically active nanoparticles according to claim 1, comprising from 1% to 15% by weight of carbonate substituted into the hydroxyapatite structure.

3. Biologically active nanoparticles according to claim 1, wherein a ratio A/B between a carbonate substitution at the hydroxyl site (A) and a carbonate substitution at the phosphate site (B) of the hydroxyapatite is comprised between 0.05 and 0.5.

4. Biologically active nanoparticles according to claim 1, wherein the carbonate substitution at the phosphate site (B) of the hydroxyapatite is greater than or equal to 65% by weight of the total carbonate present in the hydroxyapatite.

5. Biologically active nanoparticles according to claim 1, having a crystallinity degree CD comprised between 25% and 35%.

6. Biologically active nanoparticles according to claim 1, having a surface area comprised between 30 and 60 $m^2/g$.

7. Biologically active nanoparticles according to claim 1, having a substantially acicular or platelet shape having a length L comprised between 50 and 150 nm and a width W comprised between 5 and 20 nm.

8. Biologically active nanoparticles according to claim 1, further comprising an effective amount of an antibacterial ion.

9. Biologically active nanoparticles according to claim 8, comprising from 0.1 to 20% by weight with respect of the total Ca content of an antibacterial metal M ion substituted into the hydroxyapatite structure.

10. Biologically active nanoparticles according to claim 9, wherein said metal M is selected from the group consisting of Zn, Cu, Ag, and mixtures thereof.

11. Biologically active nanoparticles according to claim 9, having a molar ratio (Ca+M)/P greater than 1.7.

12. Biologically active nanoparticles according to claim 9, having the formula:

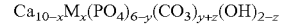

$Ca_{10-x}M_x(PO_4)_{6-y}(CO_3)_{y+z}(OH)_{2-z}$ wherein x is a number comprised between 0.0055 and 0.6, y is a number comprised between 0.065 and 0.9 and z is a number comprised between 0 and 0.32.

13. A composition comprising biologically active nanoparticles according to claim 1.

14. A composition according to claim 13, in a form suitable for oral hygiene.

15. A composition according to claim 13 or 14, in the form of suspension, oil, gel or solid.

16. A composition according to claim 15, in the form of a suspension including from 1% to 40% by weight of biologically active nanoparticles.

17. A composition according to claim 15, having a pH comprised between 7 and 8.

18. A composition according to claim 15, in the form of toothpaste, tooth powder, chewing gum for oral and dental hygiene, ointment for the gums, mouthwash, mouth bath concentrate, or gargle.

19. A composition according to claim 14, comprising a combination of biologically active nanoparticles comprising an effective amount of an antibacterial ion and biologically active nanoparticles without said ion.

20. A process for preparing an aqueous suspension including biologically active nanoparticles according to claim 1, comprising the steps of:
   a) preparing an aqueous solution or suspension comprising a Ca compound;
   b) forming nanoparticles of a carbonate-substituted hydroxyapatite by adding $PO_4^{3-}$ ions to the aqueous solution or suspension of step a) while simultaneously agitating the same over a time comprised between 30 minutes and 8 hours while maintaining said solution or suspension at a temperature lower than or equal to 60° C.;
   c) agitating the suspension of nanoparticles obtained from step b) over a time of at least two hours at a temperature lower than or equal to 60° C.

21. A process according to claim 20, wherein said Ca compound is a calcium salt selected from the group consisting of calcium hydroxide, calcium carbonate, calcium acetate, calcium oxalate, calcium nitrate, and mixtures thereof.

22. A process according to claim 20, wherein step a) is carried out in substantial absence of orally non-acceptable anions.

23. A process according to claim 20, wherein step b) is carried out while bubbling air, a $CO_2$-containing gas or a mixture thereof through the aqueous solution or suspension of step a).

24. A process according to claim 20, wherein step b) is carried out by adding an aqueous solution including $PO_4^{3-}$ ions to the aqueous solution or suspension of step a).

25. A process according to claim 24, wherein said aqueous solution including $PO_4^{3-}$ ions further comprises $HCO_3^-$ ions.

26. A process according to claim 25, wherein said aqueous solution including $HCO_3^-$ and $PO_4^{3-}$ ions is prepared by bubbling air, $CO_2$ or a mixture thereof through water to obtain a solution of carbonic acid and then adding $H_3PO_4$ thereto.

27. A process according to claim 24, wherein step b) is carried out by simultaneously adding a first solution including $CO_3^{2-}$ ions and a second solution containing $PO_4^{3-}$ ions to the aqueous solution or suspension of step a).

28. A process according to claim 20, wherein the aqueous solution or suspension of step a) has a pH comprised between 8 and 12.

29. A process according to claim 20, wherein step b) is carried out while maintaining said solution or suspension at a temperature comprised between 25° C. and 40° C.

30. A process according to claim 20, wherein the suspension obtained from step c) has a pH comprised between 7 and 8.

31. A process according to claim 20, wherein step c) is carried out while maintaining the suspension of nanoparticles at the same temperature of step b).

32. A process according to claim 20, wherein the aqueous solution or suspension of step a) further comprises an oxide or a salt of an antibacterial metal M.

33. A process according to claim 32, wherein said salt of an antibacterial metal M is an orally acceptable salt selected from the group consisting of lactates, gluconates, citrates, acetates and hydroxides.

34. A process according to claim 32, wherein step b) is carried out such that the ratio of the Ca and metal M ions contained in the solution or suspension of step a) and the $PO_4^{3-}$ ions added thereto is greater than 1.7.

35. A process for preparing biologically active nanoparticles according to claim 1, comprising the steps of:
   a) preparing an aqueous suspension including said nanoparticles by a process according to claim 20,
   b) separating solid nanoparticles from the suspension obtained from step a);
   c) drying the wet solid nanoparticles thus obtained.

36. A process according to claim 35, wherein said separation step b) is carried out by decantation, centrifugation or filtration.

37. A process according to claim 35, wherein said drying step c) is carried out by freeze-drying the wet solid nanoparticles at a temperature lower than 0° C. until reaching a constant weight.

38. A Process according to claim 35, further comprising the step of
   d) washing the separated solid nanoparticles with water or a basic solution prior to effecting said drying step c).

39. A process for manufacturing a toothpaste comprising biologically active nanoparticles according to claim 1, comprising the steps of:
   a) preparing an aqueous suspension including said nanoparticles by a process according to claim 20;
   b) mixing said aqueous suspension with other ingredients of the toothpaste.

40. A process for manufacturing a toothpaste comprising biologically active nanoparticles according to claim 1, comprising the steps of:
   a) preparing solid nanoparticles by a process according to claim 35;
   b) mixing the solid nanoparticles with other ingredients of the toothpaste.

41. A Process according to claim 39, wherein mixing step b) is carried out in a mixing apparatus maintained under a predetermined vacuum degree.

42. A Process according to claim 39, wherein mixing step b) is carried out by
   b1) mixing the aqueous suspension of step a) with other ingredients of the toothpaste except for any surfactant;
   b2) incorporating at least one surfactant into the mixture thus obtained.

43. A method of locally remineralizing the teeth comprising contacting the teeth with a composition according to claim 14.

44. A process according to claim 33, wherein step b) is carried out such that the ratio of the Ca and metal M ions contained in the solution or suspension of step a) and the $PO_4^{3-}$ ions added thereto is greater than 1.7.

45. A Process according to claim 40, wherein mixing step b) is carried out in a mixing apparatus maintained under a predetermined vacuum degree.

46. An aggregate comprising a plurality of biologically active nanoparticles according to claim 1.

47. A composition comprising aggregates of biologically active nanoparticles according to claim 1.

48. An aqueous suspension including biologically active nanoparticles according to claim 1, the aqueous suspension obtainable by:
   a) preparing an aqueous solution or suspension comprising a Ca compound;
   b) forming nanoparticles of a carbonate-substituted hydroxyapatite by adding $PO_4^{3-}$ ions to the aqueous solution or suspension of step a) while simultaneously agitating the same over a time comprised between 30 minutes and 8 hours while maintaining said solution or suspension at a temperature lower than or equal to 60° C.;
c) agitating the suspension of nanoparticles obtained from step b) over a time of at least two hours at a temperature lower than or equal to 60° C.

49. Biologically active nanoparticles according to claim 1, the biologically active nanoparticles obtainable by:

a) preparing an aqueous suspension including said nanoparticles by a process according to claim 20;
b) separating solid nanoparticles from the suspension obtained from step a);
c) drying the wet solid nanoparticles thus obtained.

* * * * *